(12) United States Patent
Lee et al.

(10) Patent No.: US 8,569,490 B2
(45) Date of Patent: Oct. 29, 2013

(54) INTERMEDIATE AND PROCESS FOR PREPARING ENTECAVIR USING SAME

(75) Inventors: Jaeheon Lee, Yongin-si (KR); Gha-Seung Park, Yongin-si (KR); Jin Hee Kim, Hwaseong-si (KR); Ji Eun Lee, Seoul (KR); Chul Hyun Park, Seongnam-si (KR); Tae Jin Choi, Seongnam-si (KR); Eun-Ju Park, Hwaseong-si (KR); Cheol Kyung Kim, Suwon-si (KR); Eun Jung Lim, Daegu (KR); Young-Kil Chang, Seoul (KR); Gwan Sun Lee, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 231 days.

(21) Appl. No.: 13/140,640

(22) PCT Filed: Dec. 24, 2009

(86) PCT No.: PCT/KR2009/007786
§ 371 (c)(1),
(2), (4) Date: Jun. 17, 2011

(87) PCT Pub. No.: WO2010/074534
PCT Pub. Date: Jul. 1, 2010

(65) Prior Publication Data
US 2011/0251387 A1    Oct. 13, 2011

(30) Foreign Application Priority Data
Dec. 26, 2008 (KR) .................... 10-2008-0134756

(51) Int. Cl.
*C07D 473/18* (2006.01)
*C07F 7/08* (2006.01)
*C07C 49/517* (2006.01)

(52) U.S. Cl.
USPC ............... 544/276; 556/436; 568/379

(58) Field of Classification Search
None
See application file for complete search history.

(56) References Cited

U.S. PATENT DOCUMENTS

| 5,206,244 A | 4/1993 | Zahler et al. |
|---|---|---|
| 5,340,816 A | 8/1994 | Zahler et al. |
| 7,034,152 B2 | 4/2006 | Pendri et al. |
| 2005/0215513 A1 | 9/2005 | Boojamra et al. |
| 2005/0272932 A1 | 12/2005 | Zhou et al. |
| 2007/0060599 A1 | 3/2007 | DiMarco et al. |

FOREIGN PATENT DOCUMENTS

| CN | 101210015 A | 7/2008 |
|---|---|---|
| CN | 101235034 A | 8/2008 |
| CN | 101245067 A | 8/2008 |
| EP | 0 481 754 A2 | 4/1992 |
| JP | 2006-509800 A | 3/2006 |
| WO | 98/09964 A1 | 3/1998 |
| WO | 2004/052310 A2 | 6/2004 |
| WO | 2008/098471 A1 | 8/2008 |

OTHER PUBLICATIONS

Zahler et al., caplus an 1992:449162.*
Taiwanese Patent Office, Taiwanese Office Action issued in corresponding TW Application No. 10120414300, dated May 1, 2012.
Ziegler et al., "Radical Cyclization Studies Directed Toward the Synthesis of BMS-200475 'Entecavir': the Carbocyclic Core," Tetrahedron, 2003, vol. 59, pp. 9013-9018.
Bisacchi et al., "BMS-200475, A Novel Carbocyclic 2'-Deoxyguanosine Analog with Potent and Selective Anti-Hepatitis B Virus Activity in Vitro," Bioorganic & Medicinal Chemistry Letters, 1997, vol. 7, No. 2, pp. 127-132.

* cited by examiner

*Primary Examiner* — Sun Jae Loewe
(74) *Attorney, Agent, or Firm* — Sughrue Mion, PLLC

(57) ABSTRACT

The present invention relates to a novel, high-yield and low-cost method for preparing entecavir, [1-S-(1α,3α,4β)]-2-amino-1,9-dihydro-9-[4-hydroxy-3-(hydroxymethyl)-2-methylenecyclopentyl]-6H-purin-6-one, an antiviral agent, and novel intermediates used therein.

10 Claims, No Drawings

INTERMEDIATE AND PROCESS FOR PREPARING ENTECAVIR USING SAME

FIELD OF THE INVENTION

The present invention relates to a novel method for preparing entecavir, an antiviral agent, and intermediates used therein.

BACKGROUND OF THE INVENTION

Entecavir, [1-S-(1α,3α,4β)]-2-amino-1,9-dihydro-9-[4-hydroxy-3-(hydroxymethyl)-2-methylenecyclopentyl]-6H-purin-6-one, is currently used for treating hepatitis B virus infection, whose structure is composed of a cyclopentane ring having purine, exomethylene, hydroxymethyl, and hydroxy substituents at the 1S-, 2-, 3R-, and 4S-positions, respectively. There have been conducted a number of studies to develop methods for preparing entecavir.

For example, U.S. Pat. No. 5,206,244 and WO 98/09964 disclose a method for preparing entecavir shown in Reaction Scheme 1:

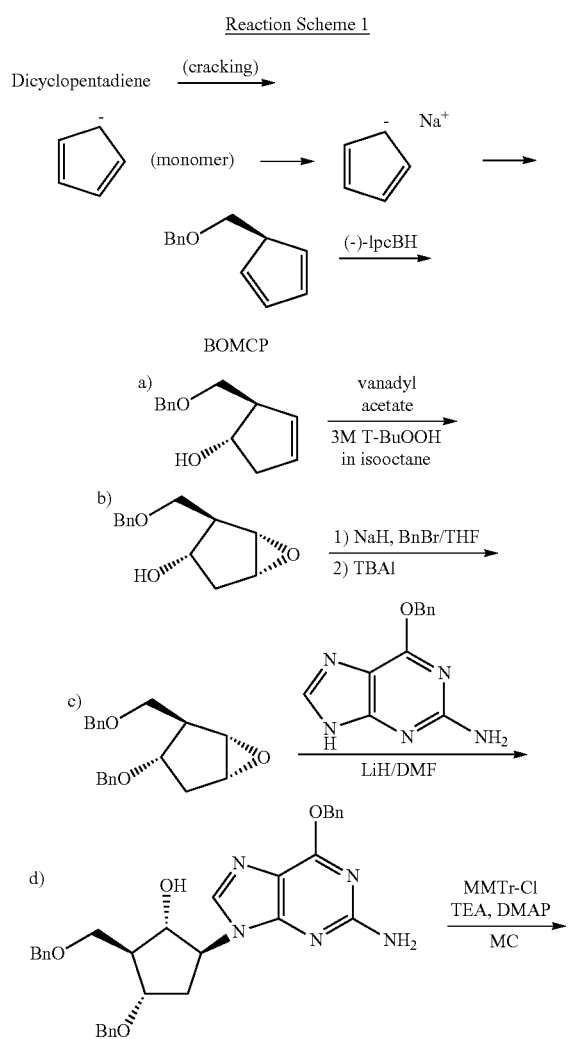

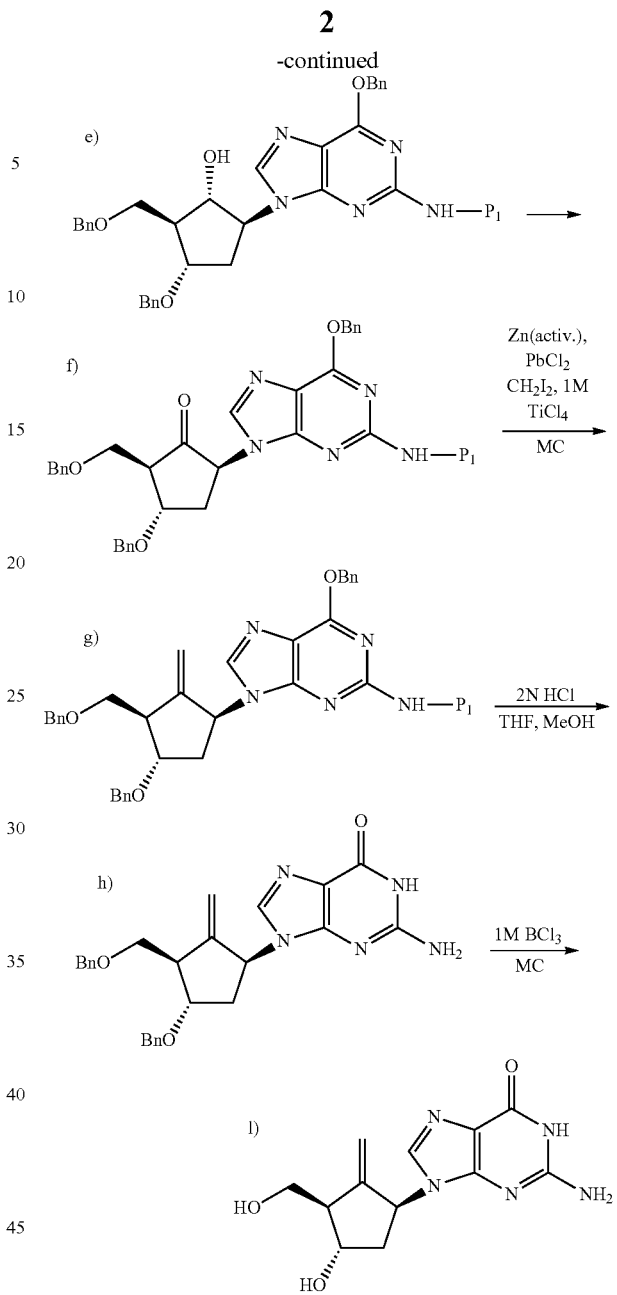

The above method, however, has difficulties in that: i) the cyclopentadiene monomer must be maintained at a temperature lower than −30° C. in order to prevent its conversion to dicyclopentadiene; ii) residual sodium after the reaction as well as the sensitivity of the reaction toward moisture cause problems; iii) the process to obtain the intermediate of formula a) must be carried out at an extremely low temperature of below −70° C. in order to prevent the generation of isomers; iv) a decantation method is required when (−)-Ipc₂BH (diisopinocampheylborane) is used for hydroboration; v) the process of the intermediate of formula a) does not proceed smoothly; and, vi) separation by column chromatography using CHP-20P resin is required to purify entecavir.

WO 2004/52310 and U.S. Pat. Publication No. 2005/0272932 disclose a method for preparing entecavir using the intermediate of formula (66), which is prepared as shown in Reaction Scheme 2:

3

Reaction Scheme 2

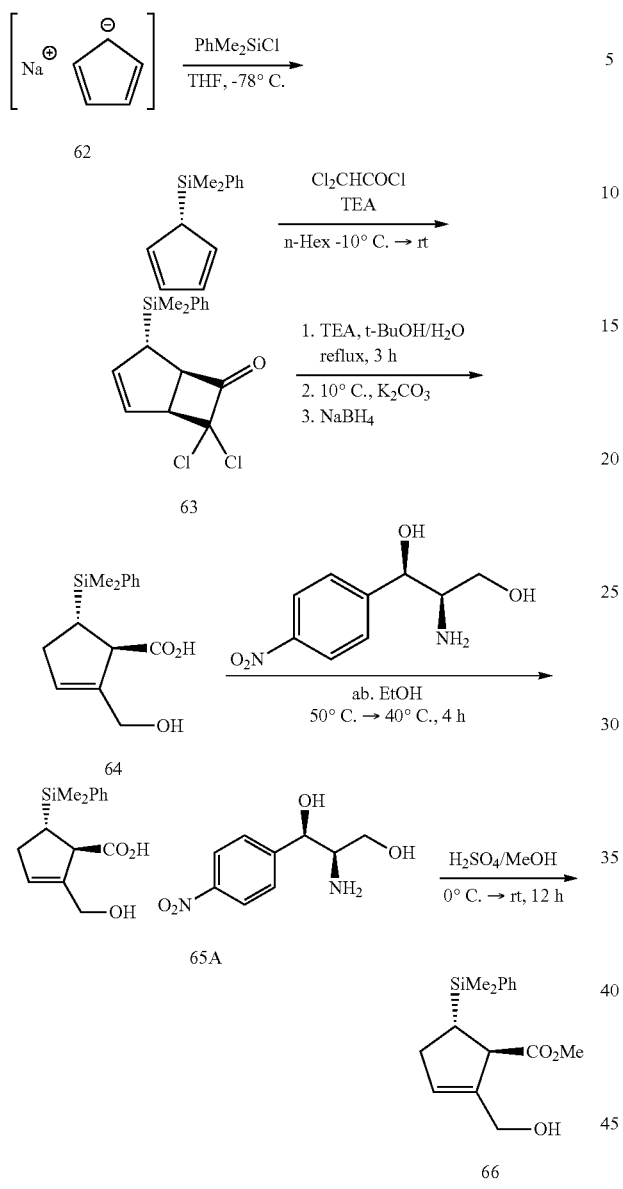

The above preparation method of the intermediate of formula (66) must be carried out at an extremely low temperature of −70° C. or less, and the yield of the desired product in the optical resolution step is less than 50%.

SUMMARY OF THE INVENTION

Accordingly, it is an object of the present invention to provide a novel and high-yield method for preparing entecavir and novel intermediates used therein.

In accordance with an aspect of the present invention, there is provided a method of preparing entecavir of formula (1), comprising the steps of (a) conducting olefination of an α-hydroxy ketone compound of formula (2) to obtain an exomethylene compound of formula (3);

(b) carrying out a Mitsunobu reaction of the exomethylene compound of formula (3) with a purine derivative to obtain a nucleoside compound of formula (4);

4

(c) removing the protecting groups of the nucleoside compound of formula (4) to obtain a compound of formula (5); and (d) hydrolyzing the compound of formula (5):

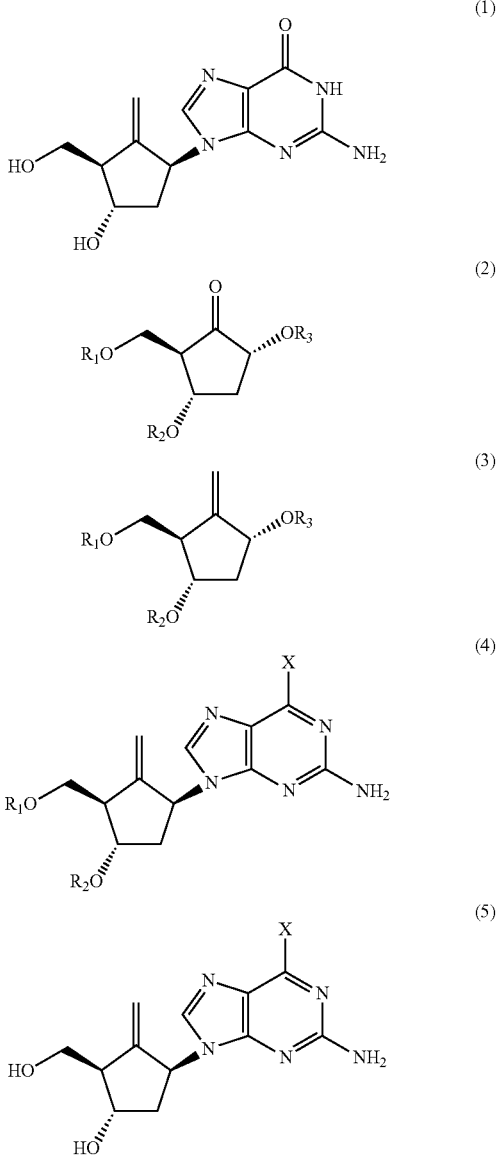

wherein $R_1$ and $R_2$ are each independently H or a hydroxy-protecting group, or $R_1$ and $R_2$ are fused together to form a cyclic hydroxy-protecting group;

$R_3$ is selected from the group consisting of H, alkylsilyl, and allylsilyl; and X is selected from the group consisting of chloro, iodo, and benzyloxy.

The compound of formula (2), which is used as a starting material in the above-mentioned method, is prepared by a method comprising the step of subjecting a ketone compound of formula (6) to a reaction with a sulfonate derivative in the presence of a base to obtain a silyl enolether of formula (7) and treating the silyl enolether of formula (7) with a peroxide:

(6)

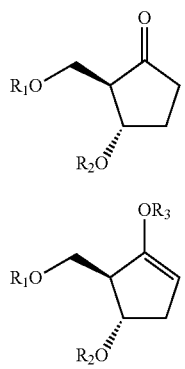

(7)

wherein R₁ to R₃ are the same as defined above.

The compound of formula (6), which is used in the preparation of the compound of formula (2), is prepared by a method comprising the steps of conducting a chiral reduction reaction of a cyclopentenone compound of formula (8) with borane dimethylsulfide in the presence of (R)-methyl-CBS (Corey-Bakshi-Shibata) catalyst to obtain a chiral cyclopentenol compound of formula (9);

subjecting the chiral cyclopentenol compound of formula (9) to a reaction with a silane derivative in the presence of a base, or removing the protecting groups of the chiral cyclopentenol compound of formula (9) followed by treating with a carbonyl or an alcohol derivative to obtain a cyclopentene compound of formula (10);

subjecting the cyclopentene compound of formula (10) to a reaction with a borane derivative to obtain a cyclopentanol compound of formula (11); and carrying out an oxidation reaction by treating cyclopentanol compound of formula (11) with 1,1,1-triacetoxy-1,1-dihydro-1,2-benziodoxol-3-(1H)-one:

(8)

(9)

(10)

(11)

wherein R₁ to R₃ are the same as defined above.

The present invention provides also an α-hydroxy ketone compound of formula (2) and a ketone compound of formula (6), which are used in the preparation of entecavir of formula (1) as an intermediate:

(2)

(6)

wherein R₁ to R₃ are the same as defined above.

The method according to the present invention makes it possible to easily prepare entecavir, an antiviral agent, from novel intermediates with a high yield and a low cost.

DETAILED DESCRIPTION OF THE INVENTION

The method for preparing entecavir according to the present invention is characterized by the steps of synthesizing a chiral ketone compound of formula (6) and using the resulting α-hydroxy ketone compound of formula (2) as an intermediate.

The term "hydroxy-protecting group" refers to, for example, trityl, benzyl, methoxybenzyl, p-nitrobenzyl, benzoyl, substituted benzoyl (e.g., alkoxybenzoyl such as methoxybenzoyl and nitrobenzoyl such as p-nitrobenzoyl), trimethylsilyl, triethylsilyl, isopropyldimethylsilyl, tert-butyldimethylsilyl, tert-butyldiphenylsilyl, thexyldimethylsilyl, allyl, methoxymethyl, (2-methoxyethoxy)methyl, and tetrahydropyranyl; preferably trityl, benzyl, and tert-butyldimethylsilyl; and most preferably trityl.

The term "cyclic hydroxy-protecting group" refers to, for example, benzylidene, naphthylidene, 4-phenylbenzylidene, cyclic acetal, cyclic ketal, cyclic carbonate, cyclic orthoester, and cyclic 1,3-(1,1,3,3-tetraisopropyl)disiloxanediyl; preferably benzylidene, naphthylidene, 4-phenylbenzylidene, and cyclic ketal; and most preferably naphthylidene.

The method for preparing entecavir of formula (1) using a cyclopentenone compound of formula (8) as a starting material according to the present invention is shown in Reaction Scheme 3, but not limited to it:

Reaction Scheme 3

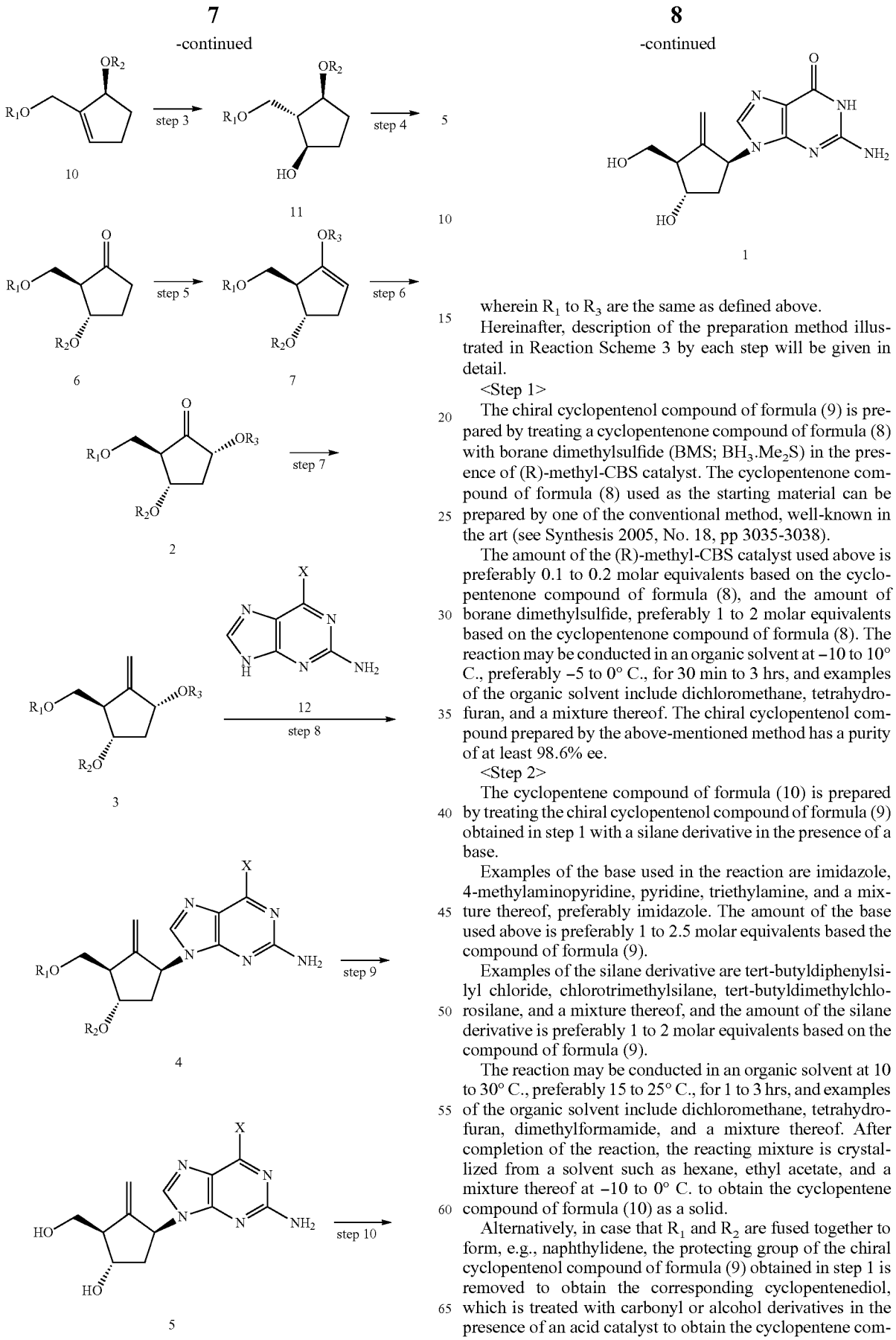

wherein $R_1$ to $R_3$ are the same as defined above.

Hereinafter, description of the preparation method illustrated in Reaction Scheme 3 by each step will be given in detail.

<Step 1>

The chiral cyclopentenol compound of formula (9) is prepared by treating a cyclopentenone compound of formula (8) with borane dimethylsulfide (BMS; $BH_3.Me_2S$) in the presence of (R)-methyl-CBS catalyst. The cyclopentenone compound of formula (8) used as the starting material can be prepared by one of the conventional method, well-known in the art (see Synthesis 2005, No. 18, pp 3035-3038).

The amount of the (R)-methyl-CBS catalyst used above is preferably 0.1 to 0.2 molar equivalents based on the cyclopentenone compound of formula (8), and the amount of borane dimethylsulfide, preferably 1 to 2 molar equivalents based on the cyclopentenone compound of formula (8). The reaction may be conducted in an organic solvent at −10 to 10° C., preferably −5 to 0° C., for 30 min to 3 hrs, and examples of the organic solvent include dichloromethane, tetrahydrofuran, and a mixture thereof. The chiral cyclopentenol compound prepared by the above-mentioned method has a purity of at least 98.6% ee.

<Step 2>

The cyclopentene compound of formula (10) is prepared by treating the chiral cyclopentenol compound of formula (9) obtained in step 1 with a silane derivative in the presence of a base.

Examples of the base used in the reaction are imidazole, 4-methylaminopyridine, pyridine, triethylamine, and a mixture thereof, preferably imidazole. The amount of the base used above is preferably 1 to 2.5 molar equivalents based the compound of formula (9).

Examples of the silane derivative are tert-butyldiphenylsilyl chloride, chlorotrimethylsilane, tert-butyldimethylchlorosilane, and a mixture thereof, and the amount of the silane derivative is preferably 1 to 2 molar equivalents based on the compound of formula (9).

The reaction may be conducted in an organic solvent at 10 to 30° C., preferably 15 to 25° C., for 1 to 3 hrs, and examples of the organic solvent include dichloromethane, tetrahydrofuran, dimethylformamide, and a mixture thereof. After completion of the reaction, the reacting mixture is crystallized from a solvent such as hexane, ethyl acetate, and a mixture thereof at −10 to 0° C. to obtain the cyclopentene compound of formula (10) as a solid.

Alternatively, in case that $R_1$ and $R_2$ are fused together to form, e.g., naphthylidene, the protecting group of the chiral cyclopentenol compound of formula (9) obtained in step 1 is removed to obtain the corresponding cyclopentenediol, which is treated with carbonyl or alcohol derivatives in the presence of an acid catalyst to obtain the cyclopentene compound of formula (10).

Examples of the acid catalyst are pyridinium p-toluenesulfonate, p-toluenesulfonic acid, and a mixture thereof, and the amount of the acid catalyst is preferably 0.1 to 0.3 molar equivalents.

Examples of the carbonyl derivative are naphthylaldehyde, naphthylaldehyde dimethylacetal, benzaldehyde, benzaldehyde dimethylacetal, 4-phenylbenzaldehyde, 4-phenylbenzaldehyde dimethylacetal, and a mixture thereof, and example of the alcohol derivative is dimethoxypropane.

<Step 3>

The cyclopentanol compound of formula (11) is prepared by treating the cyclopentene compound of formula (10) obtained in step 2 with borane derivatives.

Examples of the borane derivative used in the reaction with the cyclopentene compound of formula (10) are (+)-Ipc$_2$BH and (−)-Ipc$_2$BH, and the amount of the borane derivative is preferably 1 to 3 molar equivalents based on the cyclopentene compound of formula (10).

The reaction may be conducted in an organic solvent at −10 to 30° C., preferably 10 to 25° C., for 1 to 5 hrs, and examples of the organic solvent include dichloromethane, tetrahydrofuran, and a mixture thereof. The ratio of cyclopentanol: diastereomers in the cyclopentanol compound of formula (11) prepared by the above-mentioned method is 10:1 to 15:1.

<Step 4>

The ketone compound of formula (6) is prepared by carrying out an oxidation reaction by treating the cyclopentanol compound of formula (11) obtained in step 3 with 1,1,1-triacetoxy-1,1-dihydro-1,2-benziodoxol-3-(1H)-one.

The amount of 1,1,1-triacetoxy-1,1-dihydro-1,2-benziodoxol-3-(1H)-one used above is preferably 1 to 1.5 molar equivalents based on the cyclopentanol compound of formula (5). The oxidation reaction may be conducted in an organic solvent at 0 to 25° C., preferably 15 to 25° C., for 30 min to 2 hrs, and examples of the organic solvent include dichloromethane, tetrahydrofuran, and a mixture thereof.

<Step 5>

The silyl enolether compound of formula (7) is prepared by treating the ketone compound of formula (6) obtained in step 4 with sulfonate derivatives in the presence of a base.

Examples of the base include an amine, e.g., triethylamine, and the amount of the base is preferably 1 to 4 molar equivalents based on the ketone compound of formula (6).

Examples of the sulfonate derivative are tert-butyldimethylsilyl trifluoromethanesulfonate, trimethylsilyl trifluoromethanesulfonate, triethylsilyl trifluoromethanesulfonate, and a mixture thereof, and the amount of the sulfonate derivative is preferably 1 to 2 molar equivalents based on the ketone compound of formula (6).

The reaction may be conducted in an organic solvent at −10 to 10° C., preferably 0 to 5° C., for 30 min to 2 hrs, and examples of the organic solvent include dichloromethane, tetrahydrofuran, and a mixture thereof.

<Step 6>

The α-hydroxy ketone compound of formula (2) is prepared by treating the silyl enolether compound of formula (7) obtained in step 5 with a peroxide in a buffer solution.

Examples of the peroxide include meta-chloroperoxybenzoic acid (MCPBA), osmium tetroxide, and a mixture thereof, and the amount of the peroxide is preferably 1.5 to 2.3 molar equivalents based on the silyl enolether compound of formula (7).

Example of the buffer solution is a salt solution of sodium phosphate, disodium hydrogen phosphate, and a mixture thereof, and the amount of the salt is preferably 2 to 5 molar equivalents based on the silyl enolether compound of formula (7).

The reaction may be conducted in an organic solvent at −30 to −5° C., preferably −25 to −10° C., for 2 to 5 hrs, and examples of the organic solvent include dichloromethane, hexane, pentane, and a mixture thereof.

<Step 7>

The exomethylene compound of formula (3) is prepared by conducting olefination of the α-hydroxy ketone compound of formula (2) obtained in step 6.

The olefination is conducted by subjecting the α-hydroxy ketone compound of formula (2) to a reaction with a mixture of Nysted reagent and TiCl$_4$, a Wittig reagent, or a Tebbe reagent.

The mixture of Nysted reagent and TiCl$_4$ has preferably an 1:1 of molar rate, and the reaction may be conducted at −40 to 0° C., preferably −40 to −20° C., for 1 to 5 hrs. The amount of the reacting mixture such as the mixture of Nysted reagent and TiCl$_4$ treated with the α-hydroxy ketone compound of formula (2) is preferably 1 to 2 molar equivalents based on the α-hydroxy ketone compound of formula (2).

<Step 8>

The nucleoside compound of formula (4) is prepared by conducting a Mitsunobu reaction of the exomethylene compound of formula (3) obtained in step 7 with a purine derivative.

Examples of the purine derivative are a 2-amino-6-halopurine derivative of formula (12), a 6-O-benzylguanine derivative, and a mixture thereof, and the amount of the purine derivative is preferably 1 to 2 molar equivalents based on the exomethylene compound of formula (3). The purine derivative may be prepared by one of the conventional method well-known in the art or be commercially available.

The reaction is preferably conducted at −20 to 0° C. for 1 to 8 hrs in the presence of triphenylphosphine and diethylazodicarboxylate, and the amount of the triphenylphosphine and diethylazodicarboxylate is preferably 1 to 2 molar equivalents, respectively, based on the exomethylene compound of formula (3).

<Step 9>

The compound of formula (5) is prepared by removing the protecting groups of the nucleoside compound of formula (4) obtained in step 8.

The deprotection is conducted by one of the conventional method, well-known in the art, in detail, preferably by treating the nucleoside compound of formula (4) with 0.1 to 0.5 molar equivalents of p-toluenesulfonic acid (TsOH) based on 1 molar equivalent of the nucleoside compound of formula (4) in methanol. The reaction is preferably conducted at 20 to 25° C. for 2 to 5 hrs.

Then, the reacting mixture is treated with 1 to 3 molar equivalents tetrabutylammonium fluoride (TBAF) in tetrahydrofuran. The reaction is preferably conducted at 20 to 25° C. for 1 to 2 hrs.

<Step 10>

Entecavir of formula (1) is prepared by hydrolyzing the compound of formula (5) obtained in step 9.

The hydrolysis is performed by one of the conventional method, well-known in the art, in detail, preferably by treating with 10 to 20 molar equivalents of 2N sodium hydroxide based on the compound of formula (5) at 60 to 80° C. for 3 to 5 hrs, and, further, preferably a neutralization to pH 6.3 is performed with hydrochloric acid.

The present invention provides also the compounds of formulae (2) and (6) used as an intermediate in the preparation of entecavir.

Accordingly, the method according to the present invention makes it possible to easily prepare entecavir by using the novel compounds of formulae (2) and (6) as an intermediate with a high yield.

The following preparative examples and examples illustrate the embodiments of the present invention in more detail. However, the following preparative examples and examples of the present invention are merely examples, and the present invention is not limited thereto.

Example 1

Preparation of 3-(tert-butyl-diphenyl-silanyloxy)-2-trityloxymethyl-cyclo-pentanone (a Compound of Formula (6))

(1-1) Preparation of 2-trityloxymethyl-cyclo-2-pentenol (a Compound of Formula (9))

50 ml of anhydrous dichloromethane was added to 42.3 ml of 2M borane dimethylsulfide solution and cooled to 0° C. 4.23 ml of (R)-methyl-CBS catalyst was added thereto, and the resulting mixture was stirred for 1 hr. A solution which had been prepared by dissolving 15 g of 2-trityloxymethyl-cyclo-2-pentenone in 100 ml of anhydrous dichloromethane was added thereto dropwise over 3 hrs, before quenching the reaction mixture. 75 ml of water was added dropwise to the reaction mixture, the resulting organic layer was separated, washed with 100 ml of water, dried over anhydrous sodium sulfate, filtered, and condensed to obtain 15 g of the title compound (yield: 99%, purity: 98.6%).

NMR (300 MHz, $CDCl_3$): δ 7.70-7.23 (m, 15H), 5.87 (d, 1H), 4.78-4.75 (q, 1H), 3.92-3.77 (q, 2H), 2.52-2.48 (m, 1H), 2.30-2.23 (m, 2H), 2.12 (d, 1H), 1.82-1.74 (m, 1H).

(1-2) Preparation of tert-butyl-diphenyl-(2-trityloxymethyl-cyclo-2-pentenyloxy)-silane (a Compound of Formula (10))

7.2 g of imidazole and 16.2 ml of TBDPSCl were added successively to a solution which had been prepared by dissolving 15 g of 2-trityloxymethyl-cyclo-2-pentenol (a compound of formula (9)) obtained in (1-1) in 150 ml of dichloromethane, and the resulting mixture was stirred at room temperature for 2 hrs. After completion of the reaction, the reaction mixture was washed with 150 ml of water twice, the resulting organic layer was separated, washed with 150 ml of brine, dried over anhydrous sodium sulfate, filtered, and condensed under a reduced pressure. The residue thus obtained was dissolved in hexane and crystallized at −10° C. to obtain 24 g of the title compound as a white solid (yield: 95%).

NMR (300 MHz, $CDCl_3$): δ 7.50-7.17 (m, 25H), 6.05 (s, 1H), 4.72 (t, 1H), 3.90-3.85 (dd, 1H), 3.43-3.38 (dd, 1H), 2.50-2.30 (m, 1H), 2.20-2.05 (m, 1H), 1.95 (m, 1H), 1.73 (m, 1H), 0.91 (s, 9H).

(1-3) Preparation of 3-(tert-butyl-diphenyl-silanyloxy)-2-trityloxymethyl-cyclo-pentanol (a Compound of Formula (11))

40 g of (+)-$Ipc_2BH$ was dissolved in 90 ml of anhydrous tetrahydrofuran and cooled to 0° C. A solution which had been prepared by dissolving 30 g of tert-butyl-diphenyl-(2-trityloxymethyl-cyclo-2-pentenyloxy)-silane (a compound of formula (10)) obtained in (1-2) in 90 ml of anhydrous tetrahydrofuran was added thereto dropwise over 1 hr, and the resulting mixture was stirred at room temperature for 4 hrs.

After completion of the reaction, 67 ml of 3N aqueous sodium hydroxide was added thereto over 5 min while maintaining at the temperature of 0° C. or less. 67 ml of 30% hydrogen peroxide solution was added thereto dropwise over 40 min while maintaining at the temperature of 12° C. or less. The reaction mixture was stirred for 1 hr at the temperature of 10° C. or less, and a mixture of 150 ml of 10% sodium bisulfite and 150 ml of saturated sodium bicarbonate was added thereto to remove an excess amount of peroxide. The reaction mixture was extracted with 300 ml of ethylacetate, the resulting organic layer was separated, washed with 300 ml of sodium bicarbonate solution and 300 ml of brine, dried over anhydrous sodium sulfate, filtered, and condensed. The residue thus obtained was isolated by HPLC to obtain 26 g of the title compound as an oil (yield: 80%, ratio of cyclopentanol: diastereomer=10:1)

NMR (300 MHz, $CDCl_3$): δ 7.57-7.21 (m, 25H), 3.91-3.81 (m, 2H), 3.12 (dd, 1H), 2.74 (br, 1H), 2.68 (t, 1H), 2.34 (m, 1H), 1.77-1.72 (m, 3H), 1.53-1.48 (m, 1H), 1.01 (s, 9H).

(1-4) Preparation of 3-(tert-butyl-diphenyl-silanyloxy)-2-trityloxymethyl-cyclo-pentanone (a Compound of Formula (6))

11.9 g (28 mmol) of 1,1,1-triacetoxy-1,1-dihydro-1,2-benziodoxol-3-(1H)-one (DMP) was added to a solution which had been prepared by dissolving 14.3 g (23.3 mmol) of 3-(tert-butyl-diphenyl-silanyloxy)-2-trityloxymethyl-cyclopentanol (a compound of formula (11)) obtained in (1-3) in 150 ml of dichloromethane, and the resulting mixture was stirred at 20° C. for 30 min. The reaction mixture was washed twice with 150 ml of water, the resulting organic layer was separated, washed with 150 ml of the saturated sodium bicarbonate solution and 150 ml of brine, dried over anhydrous sodium sulfate, filtered, and condensed. The residue thus obtained was isolated by HPLC to obtain 11 g of the title compound (yield: 77.5%).

NMR (300 MHz, $CDCl_3$): δ 7.62-7.18 (m, 25H), 4.53 (q, 1H), 3.34 (dd, 1H), 3.02 (dd, 1H), 2.53 (m, 1H), 2.32 (q, 1H), 2.18 (m, 1H), 1.99-1.88 (m, 2H), 0.89 (9H).

Example 2

Preparation of 3-(tert-butyl-diphenyl-silanyloxy)-5-hydroxy-2-trityloxymethyl-cyclopentanone (a Compound of Formula (2))

(2-1) Preparation of tert-butyl-diphenyl-[3-(1,1,2,2-tetramethyl-propoxy)-2-trityloxymethyl-cyclo-3-pentenyloxy]-silane (a Compound of Formula (7))

5.4 g (8.84 mmol) of 3-(tert-butyl-diphenyl-silanyloxy)-2-trityloxymethyl-cyclo-pentanone (a compound of formula (6)) obtained in Example 1 was dissolved in 54 ml of anhydrous dichloromethane and cooled to 0° C. 4.9 ml (35.4 mmol) of triethylamine and 3 ml (13.3 mmol) of TBSOTf were added thereto dropwise successively, and the resulting mixture was stirred at 5° C. for 1 hr. After completion of the reaction, the reaction mixture was quenched by adding 54 ml of 1N aqueous hydrochloric acid. 75 ml of water was added thereto dropwise, the resulting organic layer was separated, washed with 54 ml of brine, dried over anhydrous sodium sulfate, filtered, and condensed. The residue thus obtained was isolated by HPLC to obtain 5 g of the title compound (yield: 78%).

NMR (300 MHz, CDCl$_3$): δ 7.64-6.90 (m, 25H), 4.61 (s, 1H), 4.36 (d, 1H), 2.99-2.87 (m, 2H), 2.59 (br s, 1H), 2.44 (dd, 1H), 2.15 (d, 1H), 1.04 (s, 9H), 0.88 (s, 9H), 0.17 (s, 3H), 0.11 (s, 3H).

(2-2) Preparation of 3-(tert-butyl-diphenyl-silanyloxy)-5-hydroxy-2-trityloxymethyl-cyclopentanone (a Compound of Formula (2))

1 g (1.38 mmol) of tert-butyl-diphenyl-[3-(1,1,2,2-tetramethyl-propoxy)-2-trityloxymethyl-cyclo-3-pentenyloxy]-silane (a compound of formula (7)) obtained in (2-1) was dissolved in 25 ml of dichloromethane and cooled to −25° C. 0.98 g (6.9 mmol) of disodium hydrogen phosphate and 0.71 g (3.17 mmol) of 77% meta-chloroperoxy benzoic acid (MCPBA) were added thereto successively, and the resulting mixture was stirred at −25° C. for 2.5 hrs. After formation of intermediates, 1.23 ml of sodium bisulfate solution, 1.68 g of sodium bisulfate, and 2.46 g of magnesium bisulfate were added thereto at −25° C., and the resulting mixture was stirred. The reaction mixture was heated to room temperature. After completion of the reaction, the reaction mixture was filtered with Cellite. The residue thus obtained was isolated by HPLC to obtain 0.6 g of the title compound (yield: 69.5%).
NMR (300 MHz, CDCl$_3$): δ 7.96-7.17 (m, 25H), 4.56 (q, 1H), 3.99 (q, 1H), 3.56 (dd, 1H), 3.17 (dd, 1H), 2.46-2.39 (m, 2H), 0.93 (s, 9H).

Example 3

Preparation of [1-S-(1α,3α,4β)]-2-amino-1,9-dihydro-9-[4-hydroxy-3-(hydroxymethyl)-2-methylenecyclopentyl]-6H-purine-6-one (a Compound of Formula (1))

(3-1) Preparation of 4-(tert-butyl-diphenyl-silanyloxy)-2-methylene-3-trityloxymethyl-cyclopentanol (a Compound of Formula (3))

2.4 ml (1.26 mmol) of 20% suspension Nysted reagent and 6.4 ml of tetrahydrofuran were added dropwise to a reactor successively and cooled to 0° C. 0.14 ml (1.26 mmol) of TiCl$_4$ was added thereto dropwise, and the resulting mixture was stirred. The reaction mixture was cooled to −40° C., and a solution which had been prepared by dissolving 0.527 g (0.842 mmol) of 3-(tert-butyl-diphenyl-silanyloxy)-5-hydroxy-2-trityloxymethyl-cyclopentanone (a compound of formula (2)) obtained in Example 2 in 2.4 ml of tetrahydrofuran was added thereto. The reaction mixture was stirred at room temperature for 3.5 hrs. After completion of the reaction, the reaction mixture was cooled to −20° C., quenched by adding 25 ml of 1N hydrochloric acid, and extracted with 25 ml of dichloromethane to separate an organic layer. The organic layer was washed with 20 ml of 4% sodium bicarbonate solution and 20 ml of brine successively, dried over anhydrous sodium sulfate, filtered, and condensed. The residue thus obtained was isolated by HPLC to obtain 0.184 g of the title compound (yield: 50%).
$^1$H NMR (CDCl$_3$): δ 7.64-7.60 (m, 4H), 7.38-6.90 (m, 21H), 5.35 (s, 1H), 5.11 (s, 1H), 4.34 (d, 2H), 3.03 (m, 1H), 2.91-2.77 (m, 3H), 1.78 (t, 2H), 1.03 (s, 9H).

(3-2) Preparation of 9-[4-(tert-butyl-diphenyl-silanyloxy)-2-methylene-3-trityloxymethyl-cyclopentyl]-6-chloro-9H-purine-2-yl amine (a Compound of Formula (4))

55 mg (0.088 mmol) of 4-(tert-butyl-diphenyl-silanyloxy)-2-methylene-3-trityloxymethyl-cyclopentanol (a compound of formula (3)) obtained in (3-1), 46 mg (0.176 mmol) of triphenylphosphine and 30 mg (0.176 mmol) of 2-amino-6-chloropurine were dissolved in 2.7 ml of tetrahydrofuran and cooled to −20° C. 28 μl (0.176 mmol) of diethylazodicarboxylate was added thereto. After completion of the reaction, the reaction mixture was added to 10 ml of dichloromethane, washed three times with 2.7 ml of aqueous sodium hydroxide, dried over anhydrous sodium sulfate, filtered, and condensed. The residue thus obtained was isolated by HPLC to obtain 45 g of the title compound (yield: 66.9%).
NMR (300 MHz, DMSO-d6): δ 7.82 (s, 1H), 7.61 (d, 4H), 7.49-7.34 (m, 6H), 7.26 (s, 15H), 6.69 (br s, 2H), 5.53 (t, 1H), 4.91 (s, 1H), 4.57 (s, 1H), 4.40 (s, 1H), 3.16 (t, 1H), 3.06 (t, 1H), 2.83 (s, 1H), 2.11 (d, 2H), 1.03 (s, 9H).

(3-3) Preparation of 4-(2-amino-6-chloro-purine-9-yl)-2-hydroxymethyl-3-methylene-cyclopentanol (a Compound of Formula (5))

0.131 g (0.168 mmol) of 9-[4-(tert-butyl-diphenyl-silanyloxy)-2-methylene-3-trityloxymethyl-cyclopentyl]-6-chloro-9H-purine-2-yl amine (a compound of formula (4)) obtained in (3-2) was dissolved in 2.6 ml of methanol and cooled to 0° C. 16 mg (0.084 mmol) of p-toluene sulfonic acid was added thereto, and the resulting mixture was stirred for 30 min while heating to room temperature. 16 mg (0.084 mmol) of TsOH was added thereto at room temperature, and the resulting mixture was stirred for 4 hrs. After completion of the reaction, 3 ml of water was added thereto and the reaction mixture was extracted three times with 10 ml of dichloromethane to separate an organic layer. The organic layer was dried over anhydrous sodium sulfate, filtered, and condensed. The residue thus obtained was isolated by HPLC to obtain 73 mg of [3-(2-amino-6-chloro-purine-9-yl)-5-(tert-butyl-diphenyl-silanyloxy)-2-methylene-cyclopentyl]-methanol (yield: 81%).
NMR (300 MHz, CDCl$_3$): δ 7.84 (s, 1H), 7.65 (dd, 4H), 7.45-7.35 (m, 6H), 5.50 (t, 1H), 5.21 (d, 3H), 4.84 (s, 1H), 4.52 (d, 2H), 3.72 (d, 1H), 3.45 (td, 1H), 2.72 (s, 1H), 2.59-2.49 (m, 1H), 2.25-2.18 (m, 1H), 1.09 (s, 9H).
Then, 0.27 ml (0.274 mmol) of 1M TBAF solution in tetrahydrofuran was added dropwise to a solution which had been prepared by dissolving 73 mg (0.137 mmol) of [3-(2-amino-6-chloro-purine-9-yl)-5-(tert-butyl-diphenyl-silanyloxy)-2-methylene-cyclopentyl]-methanol in 0.7 ml of tetrahydrofuran at room temperature, and the resulting mixture was stirred for 1.5 hrs. After completion of the reaction, the reaction mixture was condensed and the residue thus obtained was isolated by HPLC to obtain 34 mg of the title compound (yield: 84%).
NMR (300 MHz, MeOH-d4): δ 8.15 (s, 1H), 5.62 (t, 1H), 5.28 (t, 1H), 4.82 (t, 1H), 4.46-4.42 (m, 1H), 3.85 (dd, 2H), 3.33-3.31 (m, 1H), 2.72 (br s, 1H), 2.53-2.45 (m, 1H), 2.30-2.27 (m, 1H).

(3-4) Preparation of [1-S-(1α,3α,4β)]-2-amino-1,9-dihydro-9-[4-hydroxy-3-(hydroxymethyl)-2-methylenecyclopentyl]-6H-purine-6-one (a Compound of Formula (1))

34 mg (0.115 mmol) of 4-(2-amino-6-chloro-purine-9-yl)-2-hydroxymethyl-3-methylene-cyclopentanol (a compound of formula (5)) obtained in (3-3) was added to 0.7 ml of 2N aqueous sodium hydroxide, and the resulting mixture was stirred. The solution thus obtained was heated to 72° C. and stirred for 3.5 hrs. After completion of the reaction, the resulting mixture was cooled to 0° C., controlled to pH 6.3 by adding 2N aqueous hydrochloric acid and 1N aqueous hydrochloric acid, and condensed to obtain 24 mg of the title compound (yield: 70%, purity: 99%).

NMR (300 MHz, DMSO-d6): δ 10.58 (s, 1H), 7.67 (s, 1H), 6.42 (s, 2H), 5.36 (t, 1H), 5.11 (s, 1H), 4.86 (d, 1H), 4.83 (t, 1H), 4.57 (s, 1H), 4.24 (s, 1H), 3.54 (t, 2H), 2.53 (s, 1H), 2.27-2.18 (m, 1H), 2.08-2.01 (m, 1H).

While the invention has been described with respect to the above specific embodiments, it should be recognized that various modifications and changes may be made to the invention by those skilled in the art which also fall within the scope of the invention as defined by the appended claims.

What is claimed is:

1. A method of preparing entecavir of formula (1), comprising the steps of
    (a) conducting olefination of an α-hydroxy ketone compound of formula (2) to obtain an exomethylene compound of formula (3);
    (b) carrying out a Mitsunobu reaction of the exomethylene compound of formula (3) with a purine derivative to obtain a nucleoside compound of formula (4);
    (c) removing the protecting groups of the nucleoside compound of formula (4) to obtain a compound of formula (5); and
    (d) hydrolyzing the compound of formula (5):

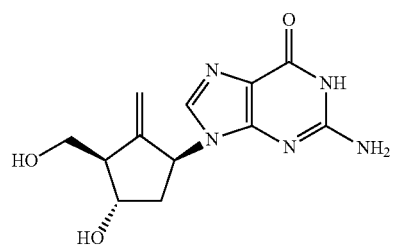

(1)

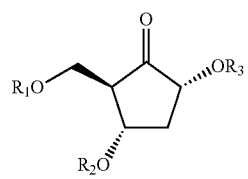

(2)

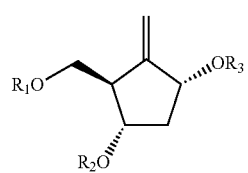

(3)

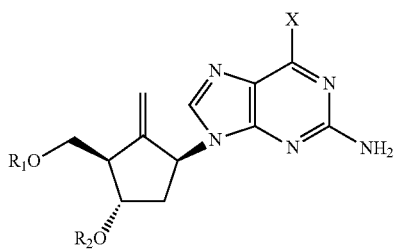

(4)

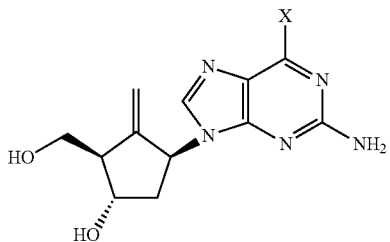

(5)

wherein
  $R_1$ and $R_2$ are each independently H or a hydroxy-protecting group, or $R_1$ and $R_2$ are fused together to form a cyclic hydroxy-protecting group;
  $R_3$ is selected from the group consisting of H, alkylsilyl, and allylsilyl; and
  X is selected from the group consisting of chloro, iodo, and benzyloxy.

2. The method of claim 1, wherein the hydroxy-protecting group is selected from the group consisting of trityl, benzyl, methoxybenzyl, p-nitrobenzyl, benzoyl, a substituted benzoyl, trimethylsilyl, triethylsilyl, isopropyldimethylsilyl, tert-butyldimethylsilyl, tert-butyldiphenylsilyl, thexyldimethylsilyl, allyl, methoxymethyl, (2-methoxyethoxy)methyl, and tetrahydropyranyl.

3. The method of claim 1, wherein the cyclic hydroxy-protecting group is selected from the group consisting of benzylidene, naphthylidene, 4-phenylbenzylidene, cyclic acetal, cyclic ketal, cyclic carbonate, cyclic orthoester, and cyclic 1,3-(1,1,3,3-tetraisopropyl)disiloxanediyl.

4. The method of claim 1, wherein the olefination is conducted by subjecting the α-hydroxy ketone compound of formula (2) to a reaction with a mixture of Nysted reagent and $TiCl_4$, a Wittig reagent, or a Tebbe reagent.

5. The method of claim 1, wherein the purine derivative is selected from the group consisting of a 2-amino-6-halopurine derivative of formula (12), a 6-O-benzylguanine derivative, and a mixture thereof:

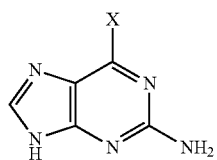

(12)

wherein X is selected from the group consisting of chloro, iodo, and benzyloxy.

6. The method of claim 1, wherein the compound of formula (2) is prepared by a method comprising the step of subjecting a ketone compound of formula (6) to a reaction with a sulfonate derivative in the presence of a base to obtain a silyl enolether of formula (7) and treating the silyl enolether of formula (7) with a peroxide:

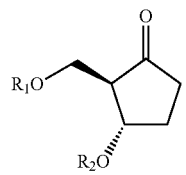

(6)

-continued

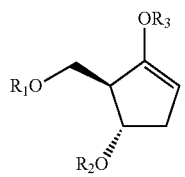

(7)

wherein $R_1$ to $R_3$ are the same as described in claim 1.

7. The method of claim 6, wherein the sulfonate derivative is selected from the group consisting of tert-butyldimethylsilyl trifluoromethanesulfonate, trimethylsilyl trifluoromethanesulfonate, triethylsilyl trifluoromethanesulfonate, and a mixture thereof.

8. The method of claim 6, wherein the compound of formula (6) is prepared by a method comprising the steps of conducting a chiral reduction reaction of a cyclopentenone compound of formula (8) with borane dimethylsulfide in the presence of (R)-methyl-CBS (Corey-Bakshi-Shibata) catalyst to obtain a chiral cyclopentenol compound of formula (9);

subjecting the resulting chiral cyclopentenol compound of formula (9) to a reaction with a silane derivative in the presence of a base, or removing the protecting groups of the chiral cyclopentenol compound of formula (9) followed by treating with a carbonyl or an alcohol derivative to obtain a cyclopentene compound of formula (10);

subjecting the resulting cyclopentene compound of formula (10) to a reaction with a borane derivative to obtain a cyclopentanol compound of formula (11); and carrying out an oxidation reaction by treating cyclopentanol compound of formula (11) with 1,1,1-triacetoxy-1,1-dihydro-1,2-benziodoxol-3-(1H)-one:

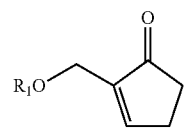

(8)

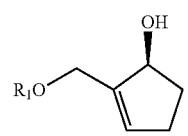

(9)

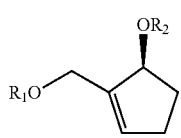

(10)

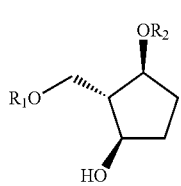

(11)

wherein $R_1$ to $R_2$ are the same as described in claim 1.

9. The method of claim 8, wherein the silane derivative is selected from the group consisting of tert-butyldiphenylsilyl chloride, chlorotrimethylsilane, tert-butyldimethylchlorosilane, and a mixture thereof.

10. The method of claim 8, wherein the carbonyl derivative is selected from the group consisting of naphthylaldehyde, naphthylaldehyde dimethylacetal, benzaldehyde, benzaldehyde dimethylacetal, 4-phenylbenzaldehyde, 4-phenylbenzaldehyde dimethylacetal, and a mixture thereof.

\* \* \* \* \*